(12) United States Patent
Crouzet et al.

(10) Patent No.: US 6,261,807 B1
(45) Date of Patent: *Jul. 17, 2001

(54) METHOD FOR PREPARING A RECOMBINANT ADENOVIRUS GENOME

(75) Inventors: Joël Crouzet, Sceaux; Laurent Naudin, Clery Saint Andre; Patrice Yeh; Cécile Orsini, both of Paris; Emmanuelle Vigne, Ivry sur Seine, all of (FR)

(73) Assignee: Rhone-Poulenc Rorer S.A., Antony (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/894,014
(22) PCT Filed: Feb. 9, 1996
(86) PCT No.: PCT/FR96/00215
  § 371 Date: Aug. 8, 1997
  § 102(e) Date: Aug. 8, 1997
(87) PCT Pub. No.: WO96/25506
  PCT Pub. Date: Aug. 22, 1996

(30) Foreign Application Priority Data

Feb. 13, 1995 (FR) .................................................. 95 01632

(51) Int. Cl.[7] .......................... C12P 19/34; C12N 15/00; C12N 7/00; C12N 1/20
(52) U.S. Cl. ................... 435/91.1; 435/320.1; 435/69.1; 435/235.1; 435/252.3
(58) Field of Search ............................... 435/69.1, 320.1, 435/235.1, 252.3, 91.1; 424/199.1, 204.1, 233.1

(56) References Cited

FOREIGN PATENT DOCUMENTS

WO 95/00655  1/1995  (WO).
WO 95/02697  1/1995  (WO).
WO 95/03400  2/1995  (WO).

OTHER PUBLICATIONS

Ketner et al, 1994, P.N.A.S. USA, vol. 91, pp. 6186–6190.*
Sternberg, 1990, GATA, vol. 7(5), pp. 126–132.*
Verma et al. Nature, Sep. 18, 1998, vol. 389, pp. 239–242.*
Ghosh–Choudhury et al., Human adenovirus cloning vectors based on infectious bacterial plasmids, Gene, 50, 161–171 (1986).
Rich et al., Development and Analysis of Recombinant Adenoviruses for Gene Therapy of Cystic Fibrosis, Human Gene Therapy, 4, 461–476 (1993).
Bett et al., An efficient and flexible system for construction of adenovirus vectors with insertions or deletions in early regions 1 and 3, Proc. Natl. Acad. Sci., USA, 91, 8802–8806 (1994).
Graham, Covalently closed circles of human adenovirus DNA are infections, The EMBO Journal, 3(12), 2917–2922 (1984).
Ketner et al., Complementation of adenovirus E4 mutants by transient expression of E4 cDNA and deletion plasmids, Nucleic Acids Research, 17(8), 3037–3048 (1989).
Natarajan et al., Proximal and distal domains that control in vitro transcription of the adenovirus IVa2 gene, Proc. Natl. Acad. Sci. USA, 81, 6290–6294 (1984).

* cited by examiner

*Primary Examiner*—Ali Salimi
(74) *Attorney, Agent, or Firm*—Finnegan, Henderson, Farabow, Garrett & Dunner, L.L.P.

(57) ABSTRACT

A novel method for preparing recombinant adenoviruses and the use of such adenoviruses in gene therapy are disclosed. Plasmids used in the construction of said adenoviruses are also disclosed.

Figure 1:
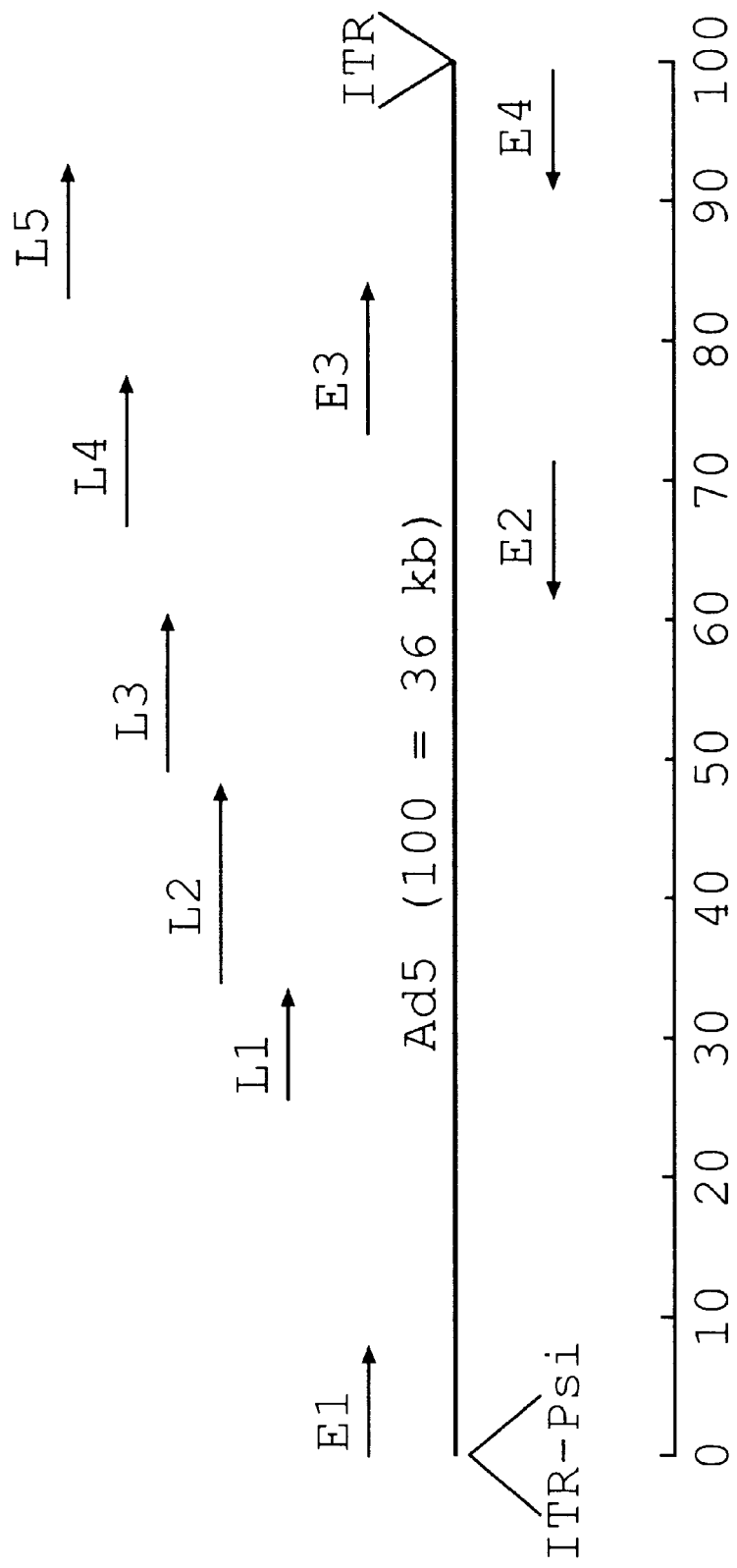

22 Claims, 18 Drawing Sheets pXL2672
21kb
-CONTAINS THE LEFT-HAND AND RIGHT-HAND REGIONS OF Ad5, FLANKED BY PacI SITES AND SEPARATED BY THE GENE FOR LEVAN SUCRASE AND THE GENE FOR RESISTANCE TO SPECTINOMYCIN
-THIS PLASMID REPLICATES IN E.COLI SF800.

pFG144
33 kb
-CONTAINS THE Ad5 ΔE1, E3 GENOME.
-THIS PLASMID DOES NOT REPLICATE IN E.COLI SF800.

CONSTRUCTION OF pXL2689 FORM OF Ad5 ΔE1, E3 WHICH REPLICATES IN E.COLI

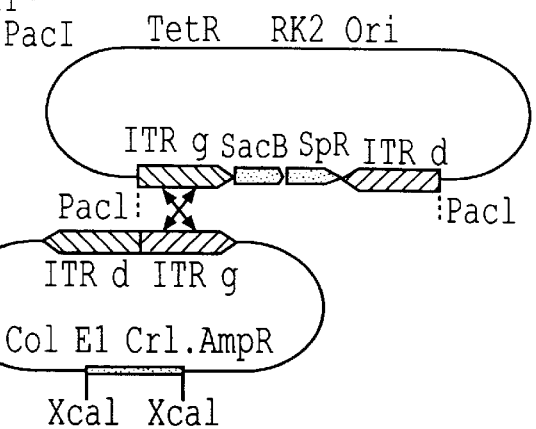

1ST RECOMBINATION: SELECTION ON TETRACYCLINE AND SPECTINOMYCIN

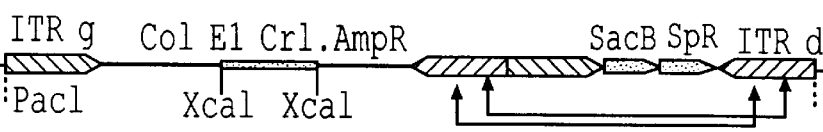

2ND RECOMBINATION: SELECTION ON TETRACYCLINE AND 5% SACCHAROSE

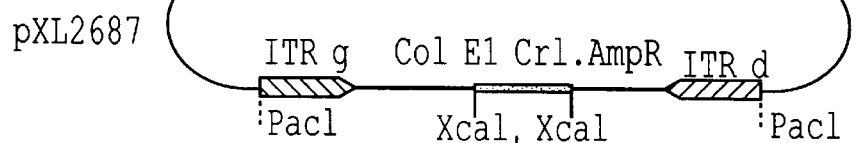

pXL2687

XbaI DELETION: DELETION OF THE ColE1 ORIGIN OF REPLICATION, SEARCH FOR A CLONE WHICH IS SENSITIVE TO AMPICILLIN.

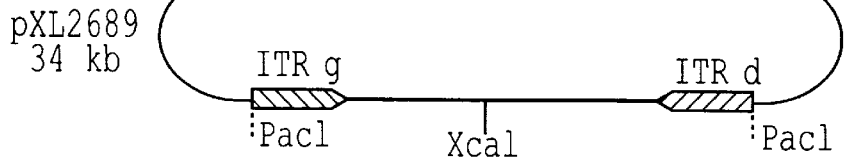

pXL2689
34 kb pXL2689, CONTAINS THE WHOLE OF THE Ad5 ΔE1, E3 GENOME. PacI DIGESTION LIBERATES A 34 kb FRAGMENT WHICH CAN BE USED DIRECTLY FOR TRANSFECTING MAMMALIAN CELLS.

FIG. 5

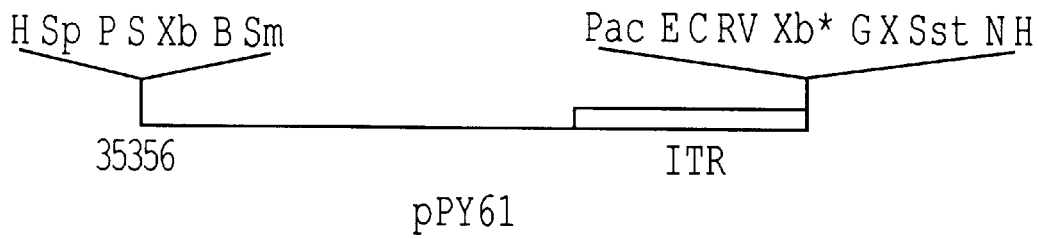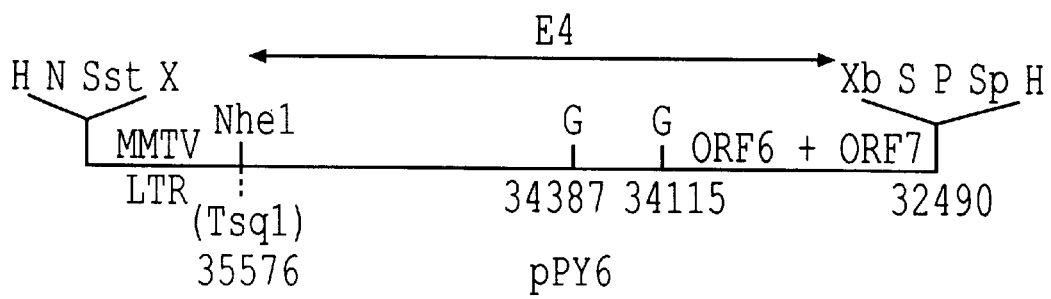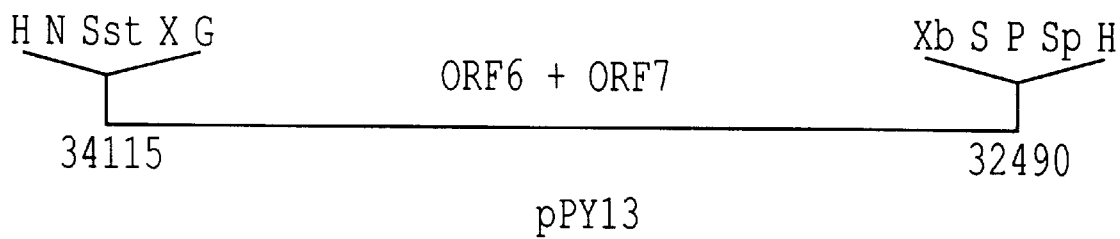
FIG. 8

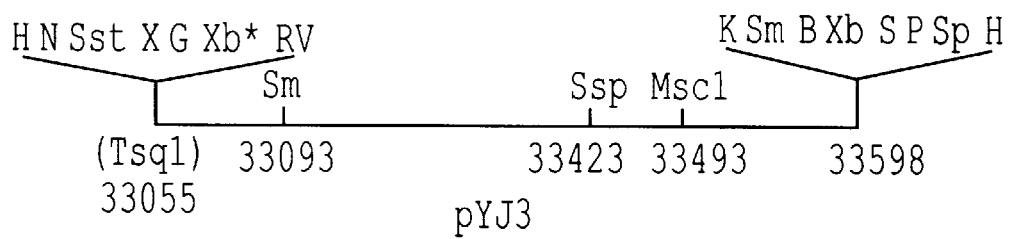
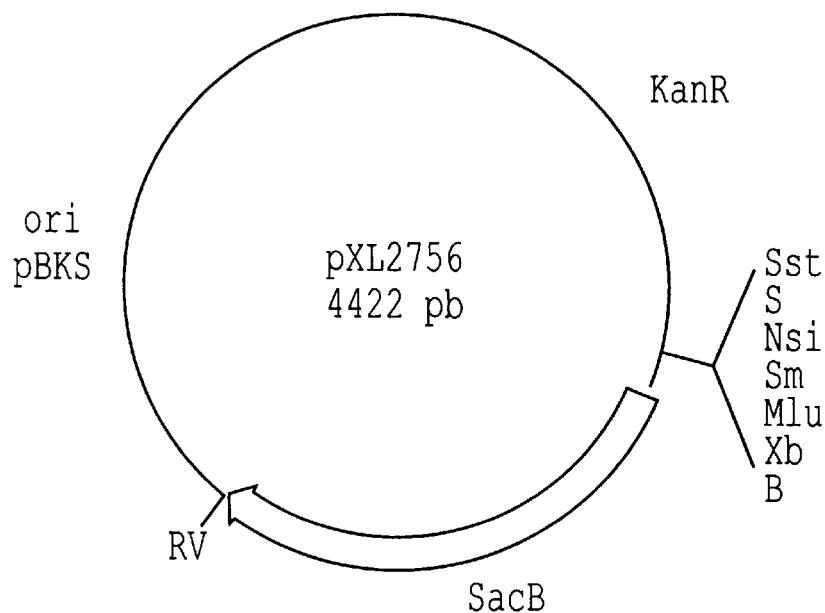
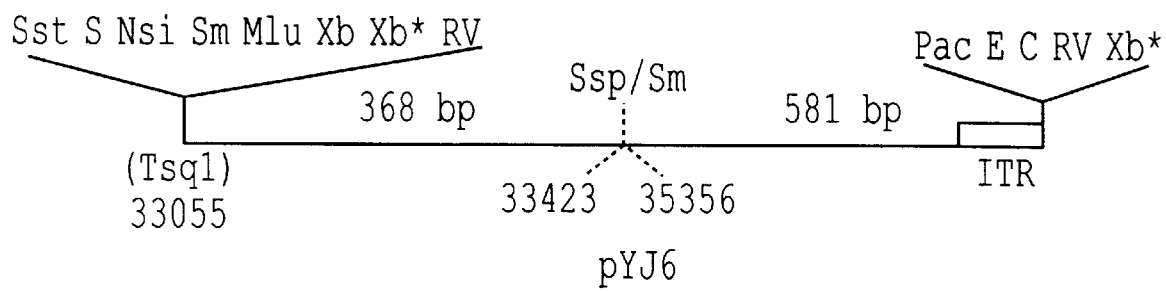
FIG. 9

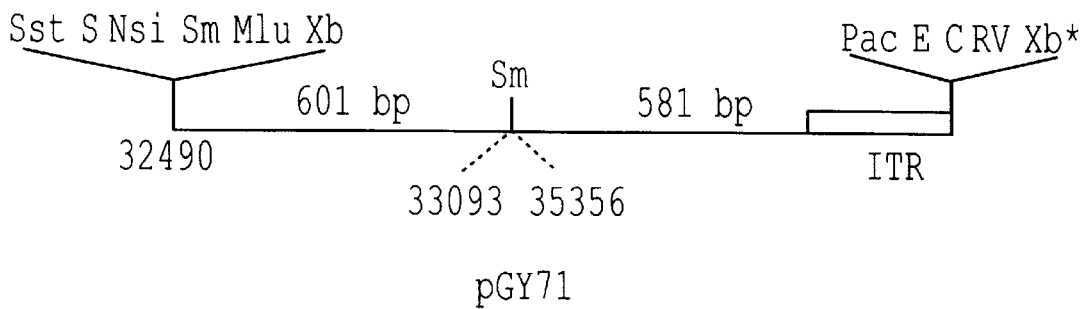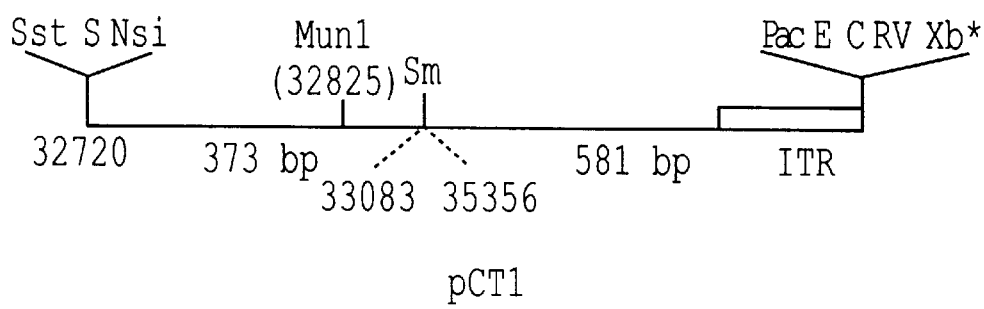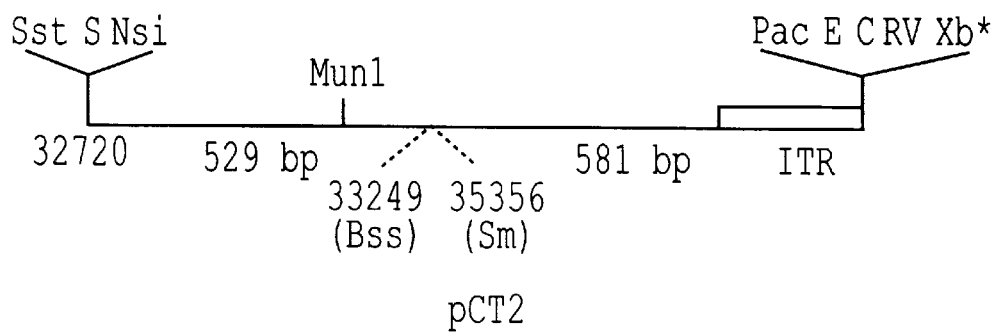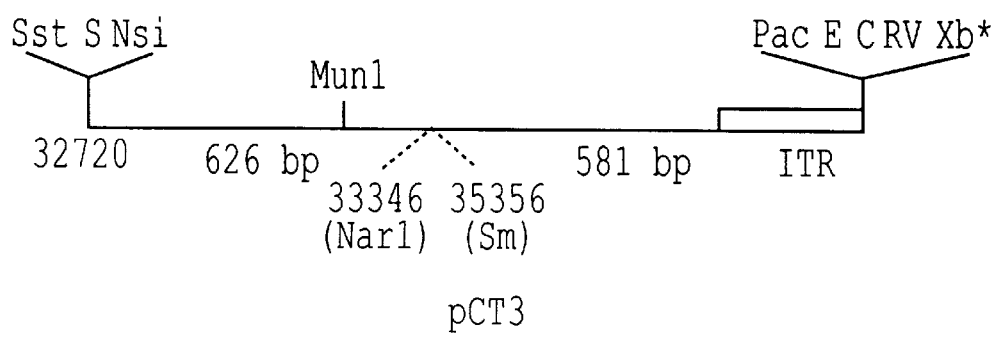
FIG. 10

Random deletions of the E4 region which are generated with ExoIII

Starting plasmid: pXL2689; E4 region, region from position 27574 to 30190 Unique XbaI site at position 25123

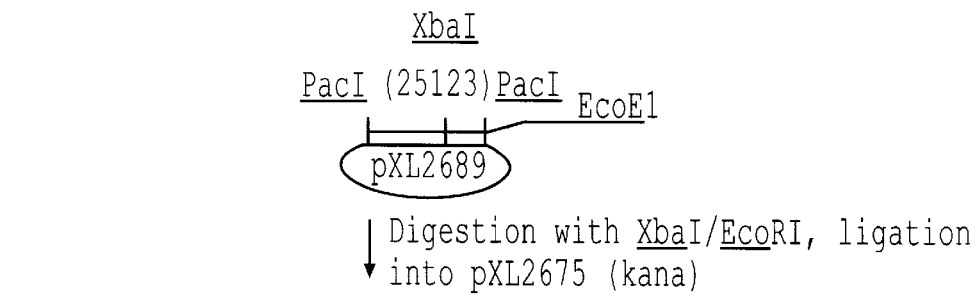

↓ Digestion with XbaI/EcoRI, ligation into pXL2675 (kana)

Creation of a second XbaI site and then introduction into the genome by means of double homologous recombination

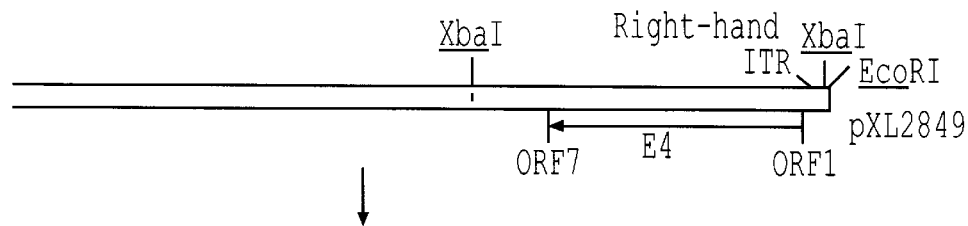

↓

Cloning of the XbaI/EcoRI fragment into a ColE1-based vector, linearization of the plasmid with selected enzymes, then digestion with ExoIII, and ligation.

↓

Estimation of the size of the deletions generated by PCR

↓

XbaI digestion of the plasmids carrying deletions. purification of fragments, and replacement, by means of cloning, of the wild-type E4 region with the deleted E4 region

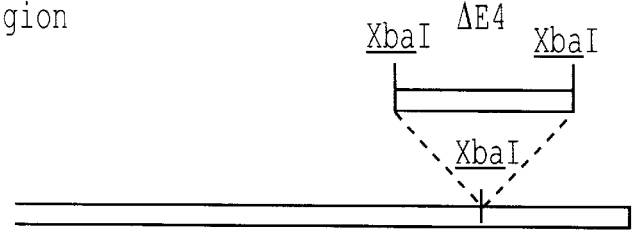

FIG. 12a

Random deletions of the E4 region which are generated with Bal31

Starting plasmid:  pXL2689; E4 region, region from position 27574 to 30190
Unique XbaI site at position 25123

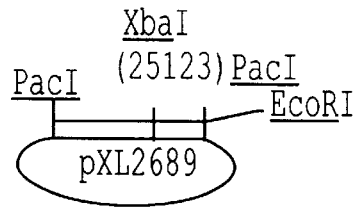

↓ Digestion with XbaI/EcoRI, ligation into pXL2675 in order to generate pXL2845

Creation of a unique CeuI site, for example, in the E4 region on the XbaI/EcoRI fragment of pXL2845

↓

Double homologous recombination in order to create the CeuI site at a predetermined position in the E4 region of pXL2689

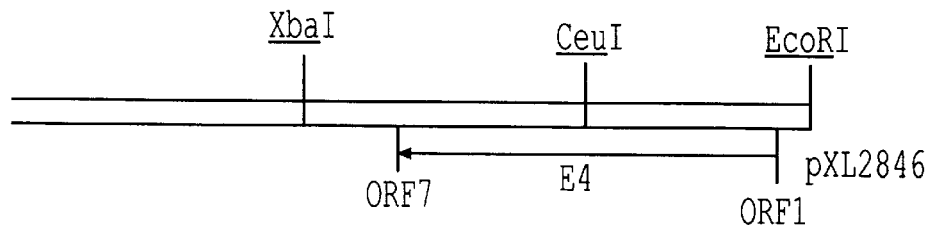

↓

Digestion with CeuI in order to linearize pXL2846, digestion with Bal31 in order to generate deletions, ligation of the deleted plasmids.

FIG. 12b

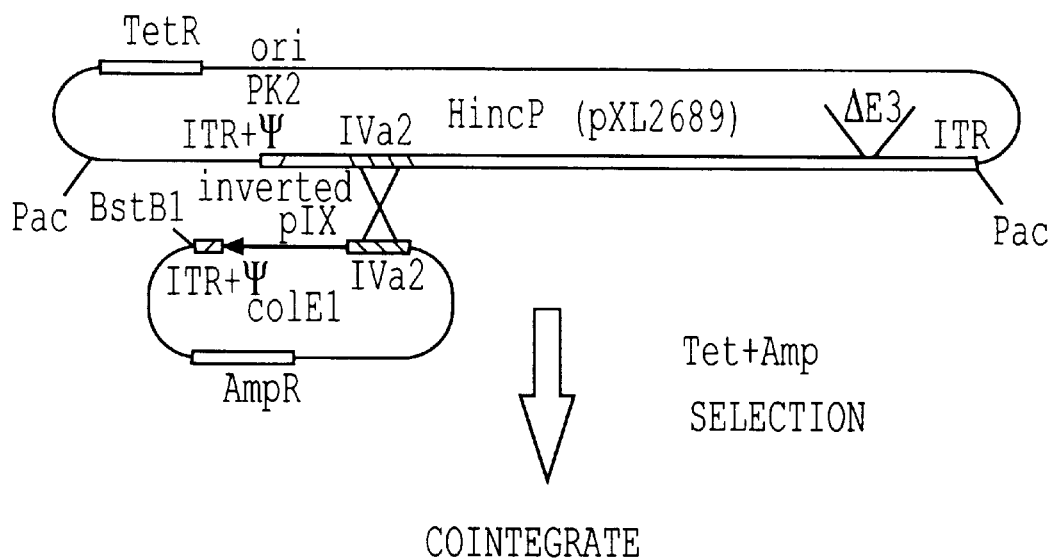
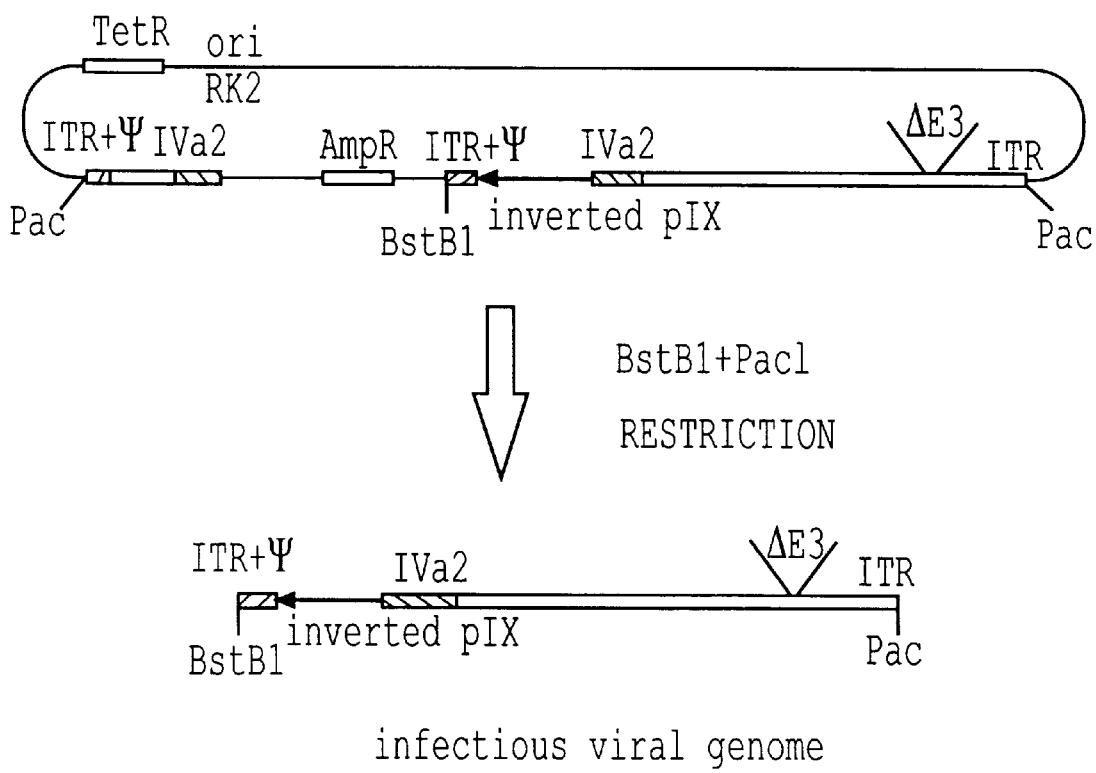
FIG. 15

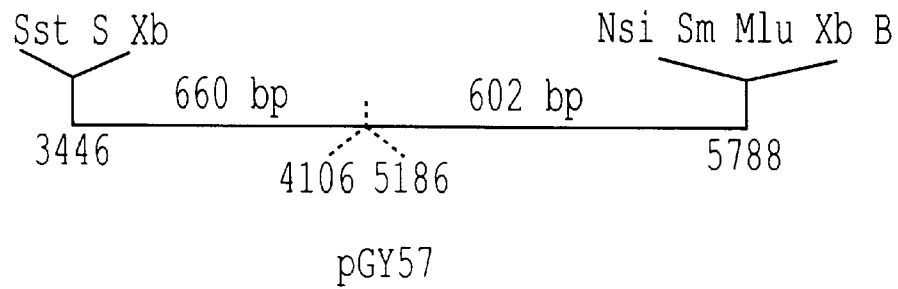
pGY57
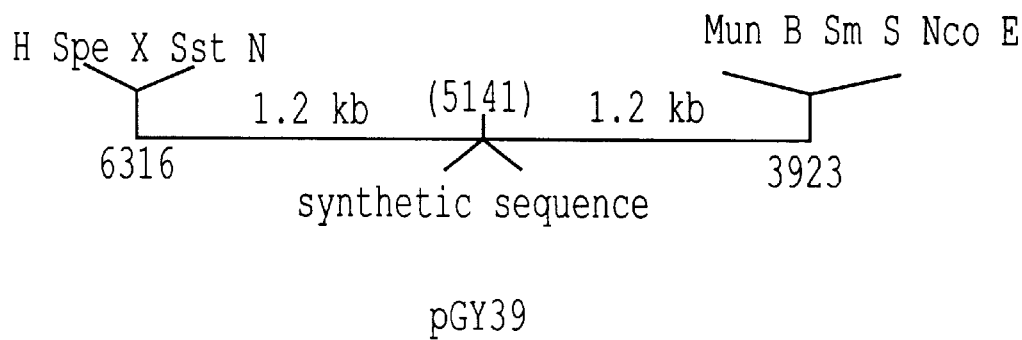
pGY39
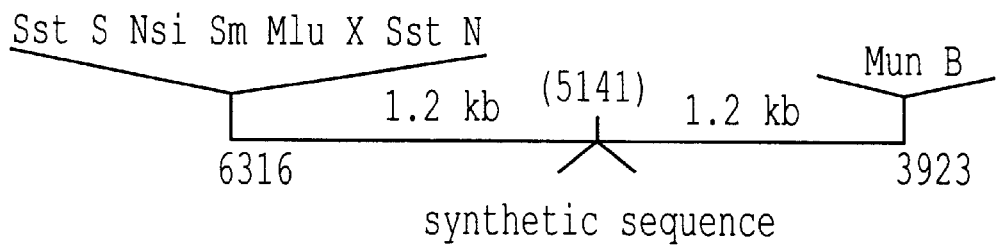
pGY52
FIG. 16

```
                           SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
          (A) LENGTH: 47 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide"

(xi) SEQUENCE DESCRIPTION: SEQ ID NO: 1:

CGGCGGGAAT TCTTAATTAA CATCATCAAT AATATACCTT ATTTTGG                 47

(2) INFORMATION FOR SEQ ID NO: 2:

(i) SEQUENCE CHARACTERISTICS:
          (A) LENGTH: 37 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide"

(xi) SEQUENCE DESCRIPTION: SEQ ID NO: 2:

CACCACCTGC AGGGCAGCCA TAACAGTCAG CCTTACC                            37

(2) INFORMATION FOR SEQ ID NO: 3:

(i) SEQUENCE CHARACTERISTICS:
          (A) LENGTH: 48 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide"

(xi) SEQUENCE DESCRIPTION: SEQ ID NO: 3:

CACCACCTGC AGGGTACCAC TAGTGTCTCC ACGTAAACGG TCAAAGTC                48

(2) INFORMATION FOR SEQ ID NO: 4:

(i) SEQUENCE CHARACTERISTICS:
```

```
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 4:

CGTGGAGACA CTAGTGGTAC CCTGCAGGGC AGCCATA                                    37
```

METHOD FOR PREPARING A RECOMBINANT ADENOVIRUS GENOME

This is a rule 371 application based on the priority date of PCT/FR96/00215 filed Feb. 9, 1996.

The present invention relates to a novel process for preparing recombinant adenoviruses and to the use of these adenoviruses in gene therapy. It also relates to prokaryotic plasmids which are suitable for preparing these adenoviruses.

Gene therapy consists in correcting a deficiency or an anomaly (mutation, aberrant expression, etc.) by introducing genetic information into the affected cell or organ. This genetic information can be introduced either in vitro, into a cell which has been removed from the organ, with the modified cell then being reintroduced into the organism, or directly in vivo into the appropriate tissue. A variety of techniques exist with regard to this second case, including various transfection techniques involving complexes of DNA and DEAE dextran (Pagano et al., J. Virol. 1 (1967) 891), of DNA and nuclear proteins (Kaneda et al., Science 243 (1989) 375), and of DNA and lipids (Felgner et al., PNAS 84 (1987) 7413), the use of liposomes (Fraley et al., J. Biol. Chem. 255 (1980) 10431), etc. More recently, the use of viruses as vectors for transferring genes has come to be seen as a promising alternative to these physical transfection techniques. In this regard, various viruses have been tested for their ability to infect specific cell populations. These viruses include, in particular, retroviruses (RSV, EMS, MMS, etc.), the HSV virus, adeno-associated viruses and adenoviruses.

Of these viruses, the adenoviruses exhibit certain properties which are attractive for use in gene therapy. In particular, they have a relatively wide host range, are able to infect quiescent cells, do not integrate into the genome of the infected cell and have not to date been associated with serious pathologies in man. As a result, adenoviruses have been used for transferring relevant genes into muscle (Ragot et al., Nature 361 (1993) 647), liver (Jaffe et al., Nature genetics 1 (1992) 372), the nervous system (Akli et al., Nature genetics 3 (1993) 224), etc.

The adenoviruses are viruses which have a linear double-stranded DNA of a size of approximately 36 kb. Their genome encompasses, in particular, an inverse repeat (ITR) sequence at each end, an encapsidation sequence (Psi), early genes and late genes (cf. FIG. 1). The principal early genes are contained in the regions E1, E2, E3 and E4. Of these, the genes contained in the E1 region are required for viral propagation. The principal late genes are contained in the regions L1 to L5. The genome of the adenovirus Ad5 has been sequenced in its entirety and is available on database (see, in particular, Genebank M73260). Similarly, parts, if not the whole, of other adenoviral genomes (Ad2, Ad7, Ad12, etc.) have also been sequenced.

In view of the properties of the adenoviruses as mentioned above, and in view of the fact that it is possible to obtain high viral titres, these viruses have already been used for transferring genes in vivo. To this end, a variety of vectors have been prepared which derive from adenoviruses and which incorporate various genes (β-gal, OTC, a-1AT, cytokines, etc.). In each of these constructs, the adenovirus has been modified in such a way as to render it unable to replicate following gene transfer. Thus, the constructs described in the prior art are adenoviruses in which the E1 and, possibly, E3 regions are deleted and into the sites of which the heterologous DNA sequences are inserted (Levrero et al., Gene 101 (1991) 195; Gosh-Choudhury et al., Gene 50 (1986) 161). Other constructs contain a deletion within the E1 region and of a non-essential part of the E4 region (WO94/12649), or a modified genomic organization (FR 94 13355).

Nevertheless, industrial and therapeutic exploitation of the adenoviruses is still limited by the current methods for preparing these recombinant viruses.

Thus, the adenoviruses are produced by transfecting the DNA of the recombinant virus into a competent encapsidating cell line. This transfection can be a straightforward transfection, when a construct is available which carries the whole of the genome of the recombinant virus, or, as is more often the case, a co-transfection of several DNA fragments which supply the different parts of the recombinant viral genome. In this case, the procedure involves one or more steps of homologous recombination between the different constructs in the encapsidating cell line in order to generate the DNA of the recombinant virus. In order to carry out one or other of these methods, it is necessary, therefore, to have available appropriate constructs which carry all or parts of the genome of the recombinant adenovirus which it is desired to produce.

Various methods, which are described in the prior art, exist for preparing these constructs in vitro. The technique which is most generally employed consists in isolating the viral DNA and then modifying it in vitro using standard molecular biological methods (digestion, ligation, etc.). The constructs which are obtained are then purified and used for transfecting the encapsidating lines. However, this technique involves producing stocks of virus and purifying viral DNA for each construct or for any manipulation of the DNA of the recombinant virus.

Another technique is based on using a plasmid which carries a part of the genome of the recombinant virus and which is co-transfected with a virus which supplies the part of the genome which is lacking. Nevertheless, as indicated above, this method involves recombination in the encapsidating line and the availability of an appropriate supplementary virus. In order to remedy these drawbacks, it has been proposed that prokaryotic plasmids be employed for preparing the viral DNAs which are to be used for the transfection. In particular, Bett et al. (PNAS 91 (1994) 8802) describes the construction of a plasmid which replicates in E. coli and which contains a modified adenoviral genome (plasmid pBHG10). More precisely, this plasmid carries an adenoviral genome in which the E1, E3 and Psi regions are deleted, which is circularized by joining the ITR sequences, and which encompasses a part of plasmid pBR322, which part is inserted within the 188–1339 region of the genome of the adenovirus. While this plasmid can be replicated in E. coli and manipulated for inserting genes of interest, it still suffers from drawbacks. In particular, its use for producing virus involves employing a second plasmid which at least supplies the left-hand region of the viral genome. Other plasmids of this type, suffering from similar drawbacks, have been described, for example by Graham (EMBOJ. 3(12) (1984) 2917). These plasmids also require a recombination step to be carried out in the encapsidating cells In particular, these technologies require different plasmids to be used in order to enable manipulation to be carried out in different regions of the adenoviral genome. Furthermore, the recombinant virus is only obtained following homologous recombination of the genomic fragments which have been co-transfected into the encapsidating cells. This accordingly limits the frequency with which the recombinant viruses are obtained, and the overall process is slow.

There exists, therefore, within the prior art, a clear need to have available suitable plasmids, which can easily be manipulated and amplified in vitro, for preparing recombinant adenoviral genomes. It is also important that the genomes which are produced in this way should be practically devoid of regions which derive from the plasmid and which are able (i) to induce an immune response, (ii) to encode resistance proteins and (iii) to reduce the capacity of the virus as a vector.

The present invention enables these drawbacks to be remedied. Thus, the present invention describes plasmids which meet all these requirements and consequently permit rapid and efficient clonal production of recombinant adenoviruses which can be used therapeutically.

More specifically, the invention relates, in the first instance, to a prokaryotic plasmid which encompasses a recombinant adenovirus genome which is flanked by one or more restriction sites which are not present in the said genome.

Figure 2:
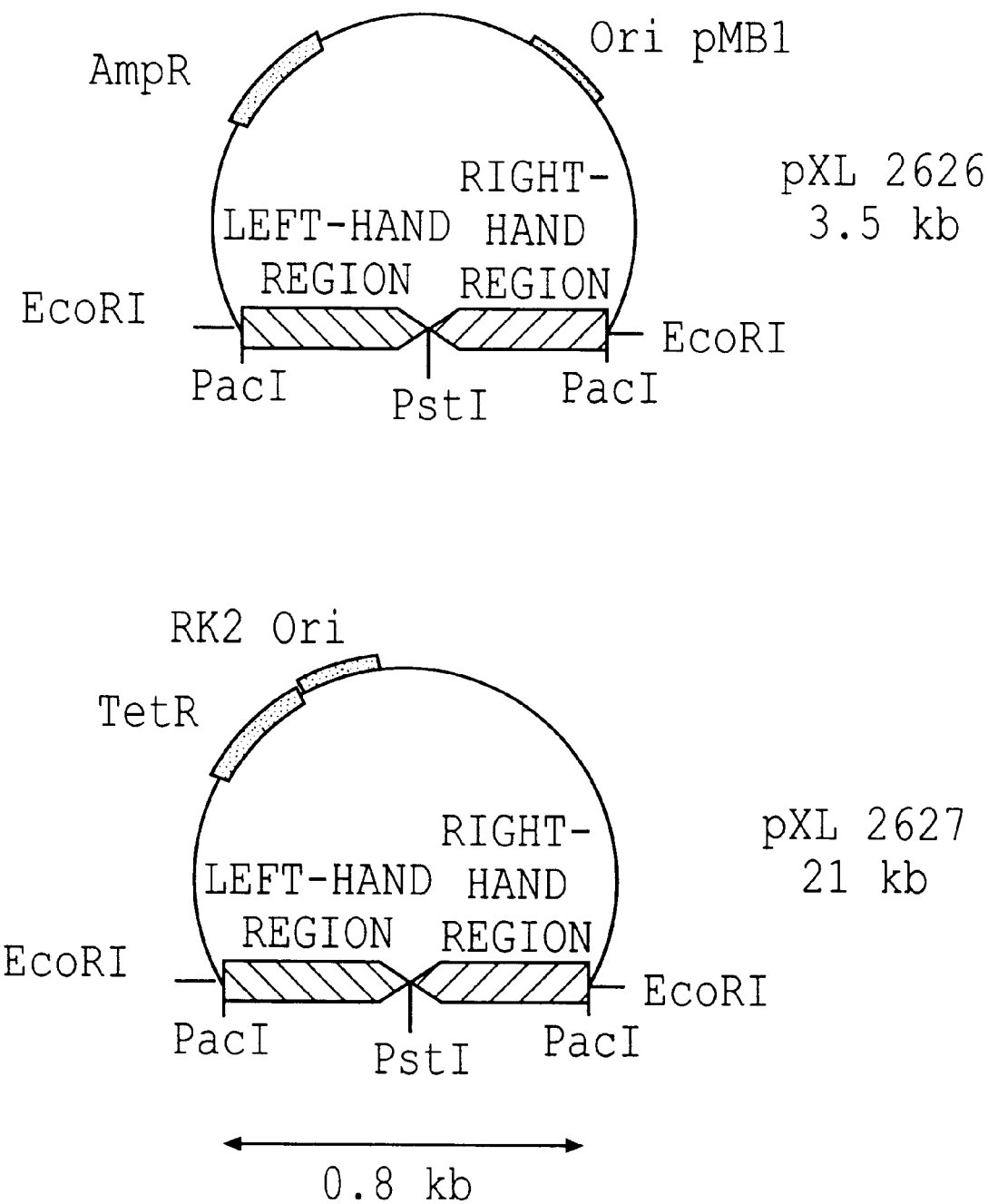

Such a plasmid is depicted, for example, in FIG. 2.

The recombinant adenovirus genome which is present in the plasmids of the invention is advantageously a complete genome. This is particularly favourable since it dispenses with the need to use a second construct supplying another part of the viral genome and with the need for the recombination step in the encapsidating line. Another advantage of the plasmids of the invention derives from the fact that the adenoviral genome is not interrupted by regions of the prokaryotic plasmid. As a result, the genomes which are produced do not contain regions of the plasmid, the drawbacks of which regions have been mentioned above. Furthermore, in the plasmids of the invention, the ITRs of the adenoviral genome are not joined, thereby enabling linear viral DNAs to be obtained which can be used directly for producing recombinant viruses.

More preferably, therefore, the plasmids of the invention encompass a first region, which enables them to be replicated in prokaryotic cells, and a second region, which contains the adenoviral genome flanked by one or more restriction sites which are not present in the said genome.

More preferably, the plasmids of the invention also encompass a region which enables prokaryotic cells containing the said plasmid to be selected. This region can consist, in particular, of any gene which confers resistance to a product, in particular to an antibiotic.

Thus, mention may be made of the genes which confer resistance to kanamycin (Kan$^r$), to ampicillin (Amp$^r$), to tetracycline (Tet$^r$) or to spectinomycin, for example, which are commonly used in molecular biology (Maniatis et al., 1989). Plasmids can be selected using other genes than the genes encoding markers for resistance to an antibiotic. In a general manner, this gene is a gene which confers on a bacterium a function which the bacterium no longer possesses (this function can correspond to a gene which has been deleted from the chromosome or rendered inactive), with the gene on the plasmid re-establishing this function. As an example, this gene can be a gene for a transfer RNA which re-establishes a deficient chromosomal function (Somoes et al., 1991).

The region which is used in the plasmids of the invention and which enables the plasmids to replicate in prokaryotic cells can be any origin of replication which functions in the chosen cells. It can be an origin of replication which is derived from a plasmid of incompatibility group P (example=pRK290) which allows replication in *E. coli* pol A strains. More generally, it can be any origin of replication which is derived from a plasmid which replicates in prokaryotic cells. This plasmid can be a derivative of pBR322 (Bolivar et al., 1977), a derivative of pUC (Viera and Messing, 1982), or of other plasmids which are derived from the same incompatibility group, that is of ColE1 or of pMB1, for example. These plasmids can, moreover, be selected from other incompatibility groups which replicate in *Escherichia coli*. They can be plasmids which are derived from plasmids belonging to incompatibility groups A, B, Fl, FII, FIII, FIV, H1, H1, I1, I2, J, K, L, N, OF, P, Q, T, U, W, X, Y, Z or 9, for example. Other plasmids can also be used, including plasmids which do not replicate in *E. coli* but replicate in other hosts such as *B. subtilis, Streptomyces, P. putida, P. aeruqinosa, Rhizobium meliloti, Aqrobacterium tumefaciens, Staphylococcus aureus, Streptomyces pristinaespiralis, Enterococcus faecium* or *Clostridium*. Preferably, use is made of origins of replication which are derived from plasmids which replicate in *E. coli*.

As previously indicated, the adenoviral genome which is present in the plasmids of the invention is advantageously a complete or functional genome, that is a genome which does not require other regions to be supplied by recombination or ligation in order to produce viral stocks in the chosen encapsidating lines.

Preferably, the recombinant adenoviral genome at least encompasses ITR sequences and a sequence which permits encapsidation.

The inverted repeat (ITR) sequences constitute the origin of replication of the adenoviruses. They are located at the ends of the viral genome (cf. FIG. 1), from where they can readily be isolated using standard molecular biological techniques which are known to the person skilled in the art. The nucleotide sequence of the ITR sequences of human adenoviruses (in particular serotypes Ad2 and Ad5) is described in the literature, as is that of canine adenoviruses (in particular CAV1 and CAV2). As far as adenovirus Ad5 is concerned, for example, the left-hand ITR sequence corresponds to the region encompassing nucleotides 1 to 103 of the genome.

The encapsidation sequence (also termed Psi sequence) is required for encapsidating the viral genome. In the genome of wild-type adenoviruses, it is located between the left-hand ITR and the E1 region (cf. FIG. 1). It can be isolated or synthesized artificially using standard molecular biological techniques. The nucleotide sequence of the encapsidation sequence of human adenoviruses (in particular serotypes Ad2 and Ad5) is described in the literature, as is that of canine adenoviruses (in particular CAV1 and CAV2). As far as adenovirus Ad5 is concerned, for example, a functional encapsidation sequence is contained between nucleotides 194 and 358 of the genome.

In one preferred embodiment of the invention, the genome of the adenovirus which is used lacks all or part of the E1 region. Thus, the E1 region is essential for viral replication and its inactivation leads to the formation of viruses which are defective for replication, that is to say are unable to replicate autonomously following gene transfer in vivo. The E1 region, or any other viral region under consideration, can be rendered non-functional by any technique known to a person skilled in the art, in particular by means of total removal, substitution, partial deletion, or the addition of one or more bases to the gene(s) under consideration. Such modifications can readily be carried out directly on the plasmids of the invention, for example, by means of genetic manipulation techniques. Advantageously, the genome of the adenovirus which is used lacks a part of the E1 region which is contained between nucleotides 454 to 3328 (PvuII-BglII fragment) or 382 to 3446 (HinfII-Sau 3A fragment).

According to a particularly advantageous embodiment, the genome of the adenovirus which is used also lacks all or part of the E3 region and/or E4 region and/or IVA2 region. The applicant has now demonstrated that it is possible to construct viruses which carry these different types of deletions. These additional deletions enhance the safety of the vector and increase its capacity.

Preferably, the adenoviral genome lacks a part of the E4 region which at least comprises open reading frames ORF3 and ORF6. The adenoviral genome can also be modified as described in application FR9413355, which is incorporated herein by reference, in such a way as to avoid the risks of contamination by replicative particles.

Preferably, the recombinant adenoviral genome also contains a nucleic acid of interest. The nucleic acid of interest can be inserted into different sites in the adenovirus genome. Advantageously, it is inserted within the E1, E3 or E4 region. However, it is obvious that other sites can be used. In particular, access to the nucleotide sequence of the genome enables the person skilled in the art to identify regions allowing insertion of the nucleic acid of interest.

The nucleic acid of interest can be any introduced DNA sequence whose transfer into and/or expression in the target cell is desired.

In particular, it can comprise one or more therapeutic genes and/or one or more genes encoding antigenic peptides.

The therapeutic genes which can thus be transferred are any gene whose transcription and, where appropriate, translation in the target cell generate products which have a therapeutic effect.

This product can be a product which is homologous with regard to the target cell (that is a product which is normally expressed in the target cell when the latter is not exhibiting any pathology). In this case, the expression enables an inadequate expression in the cell, or expression of a protein which is inactive or only weakly active due to modification, to be offset, or else enables the said protein to be overexpressed. The therapeutic gene can also encode a mutant of a cell protein, which mutant possesses enhanced stability, a modified activity, etc. The product can also be heterologous with regard to the target cell. In this case, an expressed protein can, for example, supplement or supply an activity which is deficient in the cell thereby enabling the latter to resist a pathology.

Among the therapeutic products, those which may more specifically be mentioned are enzymes, blood derivatives, hormones, lymphokines: interleukins, interferons, TNF, etc. (WO93/19191), growth factors, neurotransmitters or their precursors or enzymes for synthesizing them, trophic factors: BDNF, CNTF, NGF, IGF, GMF, aFGF, bFGF, NT3, NT5, etc; apolipoproteins: ApoAI, ApoAIV, ApoE, etc. (WO94/25073), dystrophin or a minidystrophin (FR 9111947), tumour-suppressing genes: p53, Rb, Rap1A, DCC, k-rev, etc. (WO9424297), genes encoding factors involved in coagulation: factors VII, VIII and IX, suicide genes (TK, etc.), etc.

The therapeutic gene can also be an antisense gene or sequence whose expression in the target cell enables cellular gene expression or cellular mRNA transcription to be controlled. Such sequences can, for example, be transcribed, in the target cell, into RNAs which are complementary to cellular mRNAs and hence block their translation into protein, in accordance with the technique described in patent EP 140 308.

As indicated above, the nucleic acid of interest can also be composed of one or more genes encoding an antigenic peptide which is able to induce an immune response in man. In this particular embodiment, the invention therefore enables vaccines to be produced for immunizing humans, in particular against microorganisms or viruses. The antigenic peptides can, in particular, be antigenic peptides which are specific for Epstein Barr virus, HIV virus, hepatitis B virus (EP 185 573) or pseudorabies virus, or else specific for tumours (EP 259 212).

In general, the nucleic acid of interest also encompasses sequences which enable the therapeutic gene and/or the gene encoding the antigenic peptide to be expressed in the infected cell. These sequences can be sequences which are naturally responsible for expressing the gene under consideration when these sequences are able to function in the infected cell. They can also be sequences of a different origin (responsible for expressing other proteins or even synthetic sequences). In particular, they can be promoter sequences of eukaryotic or viral genes. For example, they can be promoter sequences which are derived from the genome of the cell which it is desired to infect. Similarly, they can be promoter sequences which are derived from the genome of a virus, including the adenovirus which is used. In this regard, the promoters of the E1A, MLP, CMV, RSV etc. genes may, for example, be mentioned. Furthermore, these expression sequences can be modified by adding activation sequences, regulatory sequences, etc. Moreover, when the inserted gene does not include any expression sequences, it can be inserted into the genome of the defective virus downstream of such a sequence. Finally, the nucleic acid of interest can also include, in particular upstream of the therapeutic gene, a signal sequence which directs the synthesized therapeutic product into the secretory pathways of the target cell. While this signal sequence can be the natural signal sequence of the therapeutic product, it can also be any other functional signal sequence, or an artificial signal sequence.

The plasmids of the invention can be constructed using adenoviruses of varying origin. Thus, a variety of adenovirus serotypes, whose structure and properties vary to some extent, have been characterized. Of these serotypes, preference is given to using, within the scope of the present invention, human type 2 or type 5 adenoviruses (Ad 2 or Ad 5) or adenoviruses of animal origin (see application WO 94/26914). Of the adenoviruses of animal origin which can be used within the scope of the present invention, those which may be mentioned are adenoviruses of canine, bovine, murine, (example: Mav1, Beard et al., Virology 75 (1990) 81), ovine, porcine, avian and also simian (example: SAV) origin. Preferably, the adenovirus of animal origin is a canine adenovirus, more preferably a CAV2 adenovirus [Manhattan or A26/61 strain (ATCC VR-800), for example].

According to one particular embodiment of the invention, the adenovirus which is used is an adenovirus of human origin. According to another advantageous embodiment, the adenovirus is an adenovirus of animal origin.

As indicated above, the recombinant adenovirus genome is advantageously flanked by one or more restriction sites which are not present in the said genome. This or these sites enable the recombinant adenoviral genome to be excised from the plasmid in a simple and efficient manner. Since the genomic sequence of the adenovirus is known and accessible, the person skilled in the art can select, by means of routine experiments, restriction sites which are not present in this genome. The PacI, NspV and SwaI (for Ad5) or SnabI (in the case of Ad2) sites may be mentioned by way of example. It is also possible to render certain sites unique by modifying the sequence of the adenoviral genome. Thus, other enzymes can be used if the corresponding restriction sites are removed, modified or deleted in the adenoviral sequence which is constructed in E. coli. The sites can be positioned directly adjacent to the ends of the adenoviral genome or separated from them by a few base pairs.

A plasmid which is particularly preferred within the meaning of the invention is the plasmid pXL2638, which encompasses the origin of replication of plasmid RK2, the gene for resistance to tetracycline, and a recombinant adenovirus genome whose E1 and E3 regions are non-functional and which is flanked by 2 PacI sites. A nucleic acid of interest can be inserted into different sites in the adenoviral genome, in particular within the E1, E3 and E4 regions. Various restriction sites can be used for this purpose, such as, in particular, the XbaI site.

The plasmids of the present invention can be constructed in different ways. According to a preferred method, fragments carrying the ITRs of the adenoviral genome, flanked by appropriate restriction site(s), are initially constructed. These ITRs are next introduced into a prokaryotic plasmid and then, in a third step, the recombinant adenoviral genome is reconstructed between the ITRs, either by ligation or by recombination. Preferably, the genome is reconstructed by recombination between the desired recombinant adenoviral genome and the homologous regions (encompassing the ITRs and the flanking regions) of the plasmid.

More specifically, the genome can be reconstructed in E. coli using a polA strain in order to select the homologous recombination events. It is evident that these constructs can also be effected in the absence of systems for selecting recombination events. Thus, such recombination events can be screened for by minipreparation, loss or acquisition of a marker, or even screening with the aid of specific radioactive probes for junctions which are obtained or lost. Furthermore, other techniques exist for selecting homologous recombination events in E. coli. Those which may be mentioned are the use of replication-thermosensitive plasmids (Hamilton et al., 1989), the use of non-replicative circular molecules (described, for example, by Slater and Maurer, 1993), the use of strains in which the vector which is employed does not replicate (Miller and Mekalanos, 1988, Zeef et al., 1994), etc. All these systems can be used in place of polA strains and transformation with a plasmid which is derived from pBR322 or its numerous derivatives, or from other plasmids whose replication is PolA-dependent or even from plasmids which do not replicate in Escherichia coli.

The present application also relates to any prokaryotic cell which harbours a plasmid such as defined above. This prokaryotic cell can, in particular, be any bacterium for which a vector system exists into which recombinant DNA can be introduced. Escherichia coli, Salmonella typhimurium, Bacillus subtilis, Pseudomonas putida, Pseudomonas aeruginosa, Agrobacterium tumefaciens, Rhizobium meliloti or the bacteria of the Streptomyces genus may be mentioned by way of example. These cells are advantageously obtained by transformation using the techniques known to the person skilled in the art. The transformation can, in particular, be effected by means of the transformation technique using $CaCl_2$ (Dagert and Ehrlich, 1979), or by means of that developed by Hanahan et al. (1983) or any technique derived from this (Maniatis et al., 1989), as well as by means of electrotransformation (Wirth et al., 1989). See also the general molecular biological techniques above.

The present invention also relates to a process for producing recombinant adenovirus genomes. According to this process, prokaryotic cells such as described above are cultured and then, in a second step, the plasmids are recovered. Advantageously, the cultivation is carried out over a period of time which is sufficiently long to produce appropriate quantities of plasmid. The plasmid can be recovered by any technique known to the person skilled in the art for preparing plasmid DNA. Thus, it can be recovered by preparing a clear lysate followed by centrifugation in a caesium chloride gradient (Maniatis et al., 1989). Other techniques, which resort to other methods of lysis using triton X-100, for example (Ausubel et al., 1987), can be employed, or else an anion exchange column can be employed after the lysis step and the step for separating the plasmid DNA from the majority of the chromosomal DNA and the proteins. The plasmids which have been recovered in this way can then be purified and treated in the presence of the restriction enzyme which corresponds to the sites flanking the viral genome. This enables a linear recombinant adenovirus genome, which can be used directly for the clonal production of recombinant viruses, to be generated in a single step.

In this respect, a first method for preparing the recombinant viruses consists in transfecting the viral genome which is produced from the plasmids of the invention into a competent encapsidating cell line, that is a cell line which carries in trans all the functions which are required for complementing the defective virus. These functions are preferably integrated into the genome of the cell, thereby reducing the risks of recombination and conferring enhanced stability on the cell line.

A second approach consists in co-transfecting the recombinant genome which has been prepared and the DNA of one or more helper viruses or plasmids into an appropriate cell line. When this method is used, it is not necessary to have available a competent cell line which is able to complement all the functions of the recombinant adenovirus which are defective. Thus, some of these functions are complemented by the helper virus (es) This or these helper virus(es) is/are itself/themselves defective.

Of the cell lines which can be used, that which may, in particular, be mentioned is the human embryonic kidney line 293 (Graham et al., J. Gen. Virol. 36 (1977) 59). This line contains, in particular, integrated into its genome, the left-hand part of the genome of the human Ad5 adenovirus (12%). The transfection can advantageously be carried out directly using the plasmid digestion product which was obtained in accordance with the process described above, without any step for purifying the adenoviral genome.

The present invention also relates to any pharmaceutical composition which comprises one or more recombinant adenoviruses prepared in accordance with this process. The pharmaceutical compositions of the invention can be formulated with a view to administering them by the topical, oral, parenteral, intranasal, intravenous, intramuscular, subcutaneous, intraocular, transdermal, etc. route.

Preferably, the pharmaceutical composition contains excipients which are pharmaceutically acceptable for an injectable formulation. These excipients can, in particular, be sterile, isotonic salt (monosodium and disodium phosphate, sodium, potassium, calcium or magnesium chloride, etc., or mixtures of such salts) solutions, or dry, in particular lyophilized, compositions which, by adding, as the case may be, sterilized water or physiological saline to them, enable injectable solutions to be constituted.

The doses of virus which are employed for the injection can be adjusted in accordance with different parameters in particular in accordance with the mode of administration which is used, the pathology concerned, the gene to be expressed or alternatively the desired duration of the treatment. In a general manner, the recombinant adenoviruses of the invention are formulated and administered in the form of doses containing between $10^4$ and $10^{14}$ pfu, preferably from $10^6$ to $10^{10}$ pfu. The term pfu ("plaque-forming unit") corresponds to the infective power of a virus solution and is determined by infecting a suitable cell culture and measuring, generally after 15 days, the number of plaques of infected cells. The techniques for determining the pfu titre of a viral solution are well documented in the literature.

Depending on the heterologous DNA sequence which is inserted, the adenoviruses of the invention can be used for treating or preventing numerous pathologies, including genetic diseases (dystrophy, cystic fibrosis, etc.), neurodegenerative diseases (Alzheimer's, Parkinson's, ALS, etc.), cancers, pathologies associated with disorders of coagulation or wih dyslipoproteinaemias, pathologies associated with viral infections (hepatitis, AIDS, etc.), etc.

The present invention will be more fully described with the aid of the examples which follow and which should be considered as being illustrative and not limiting.

FIGURE LEGENDS

FIG. 1: Genetic organization of adenovirus Ad5

FIG. 2: Restriction maps of pXL2626 and pXL2627. Amp$^r$: gene for resistance to ampicillin; pMB1 Ori, origin of replication of pMB1; Tet$^r$, gene for resistance to tetracycline; RK2 Ori, origin of replication of plasmid RK2. The circular parts of the plasmid maps are not on the same scale as that of 0.8 kb which is indicated for the 2 ITRs.

Figure 3:
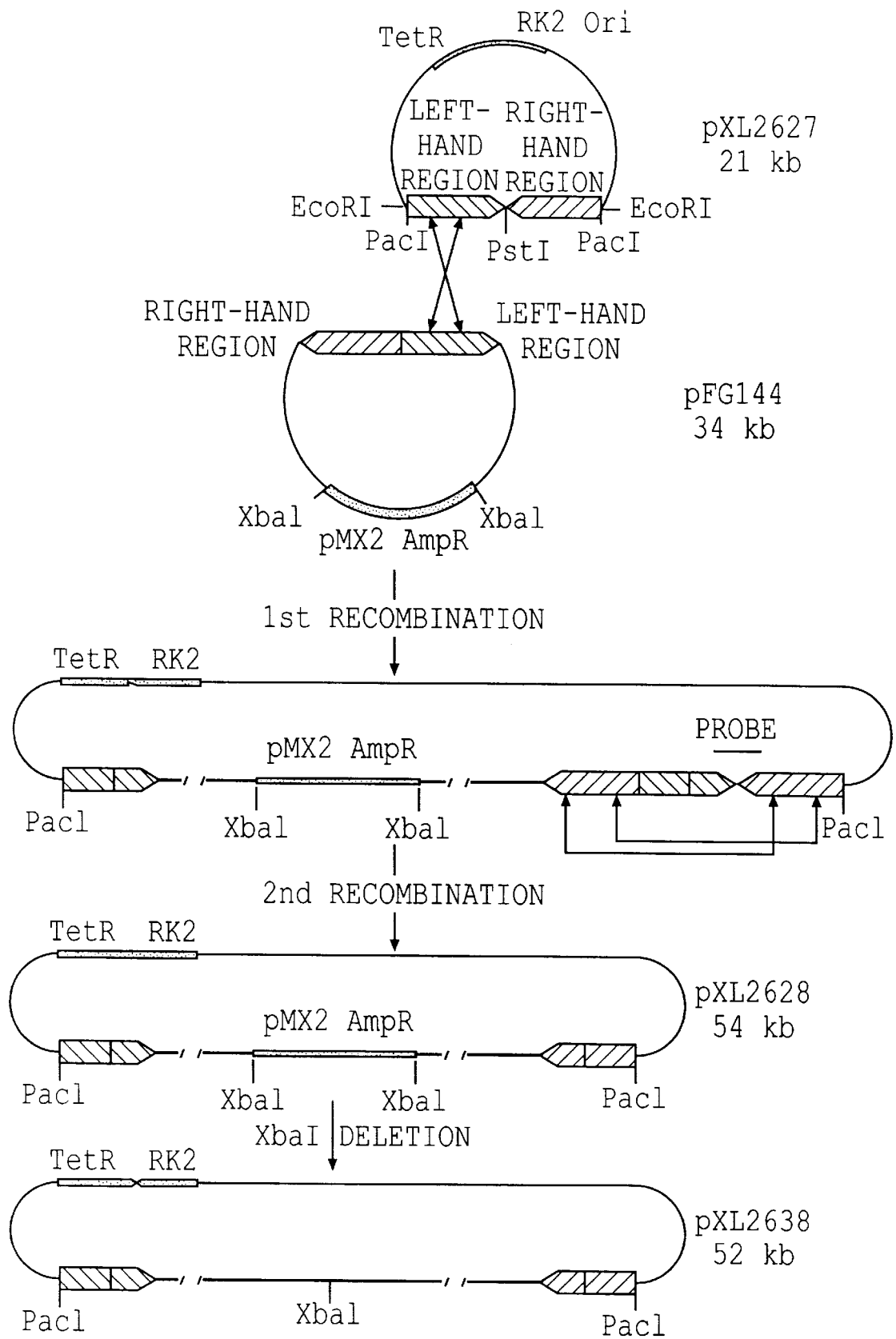

FIG. 3: Construction of plasmid pXL2638.
This construction is carried out, as described in Example 1–2, by means of homologous recombination in SF800 (*E. coli* polA). Amp$^r$: gene for resistance to ampicillin; pMB1 Ori, origin of replication of pMB1; Tet$^r$, gene for resistance to tetracycline; RK2 Ori, origin of replication of plasmid RK2. The circular parts of the plasmid maps and the adenoviral sequences are not on the same scale.

Figure 4:
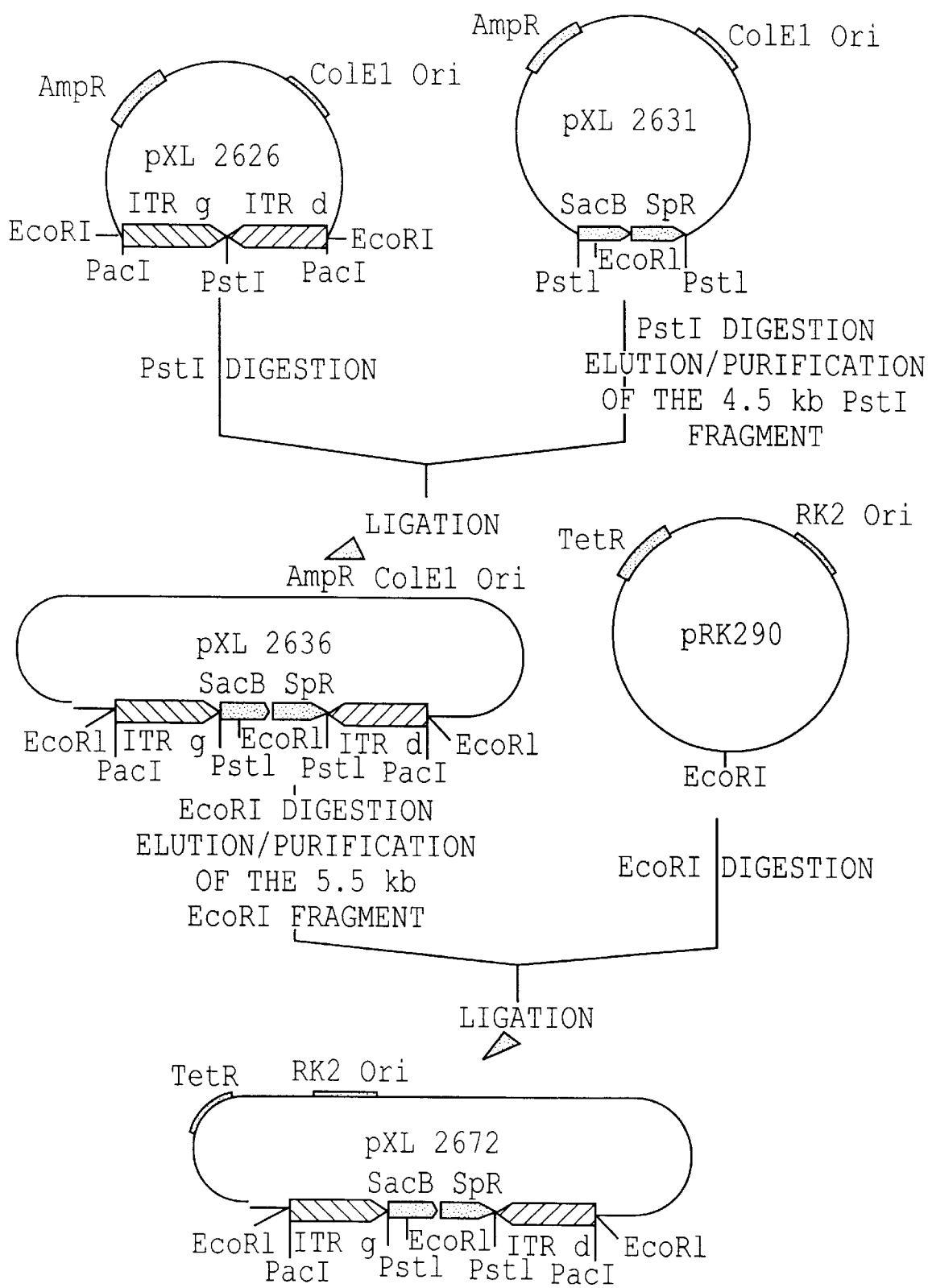

FIG. 4: Construction of pXL2672.

FIG. 5: Construction of pXL2689 from of Ad5 ΔE1, E3,which replicates in *E. coli*.

Figure 5A:
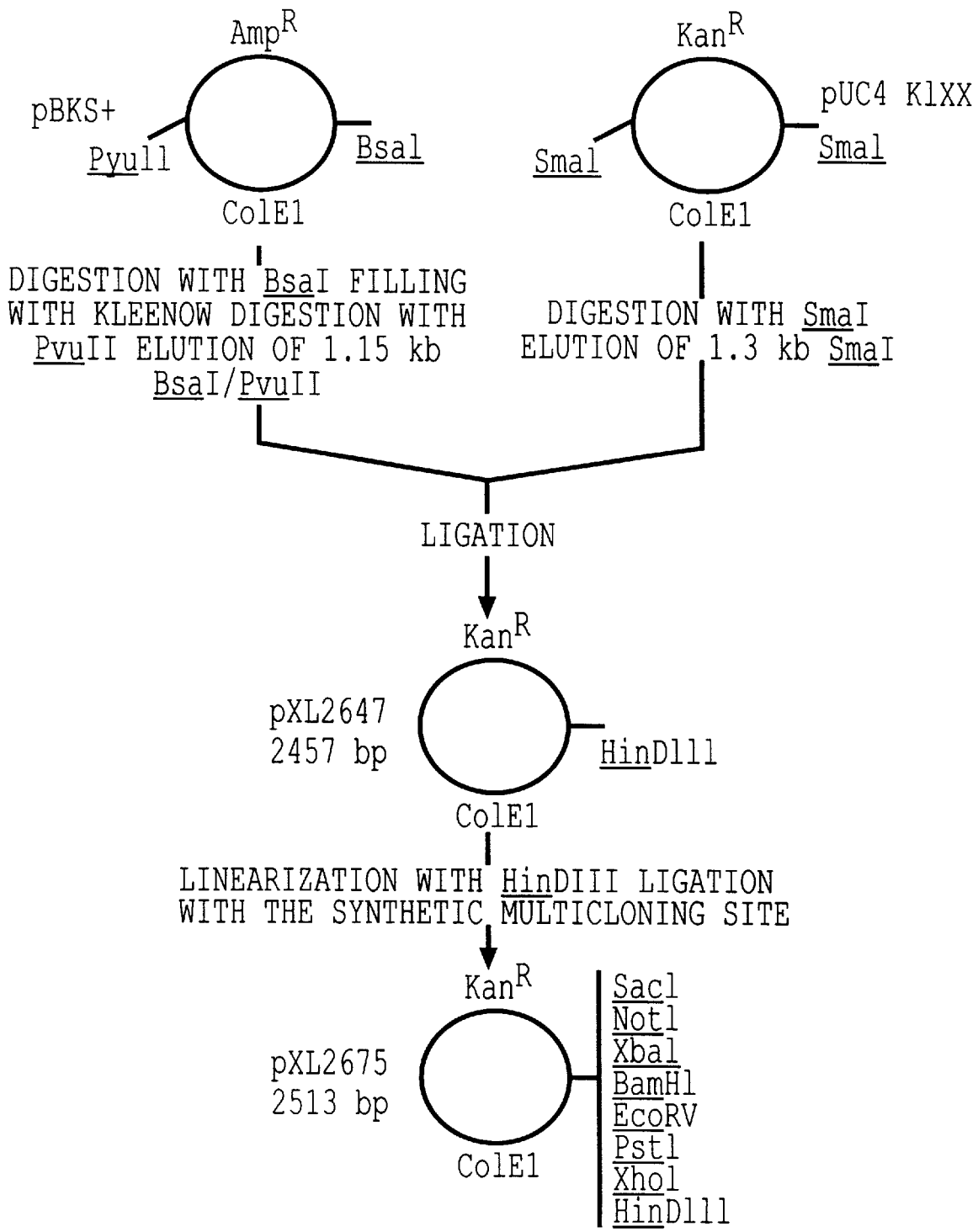

FIG. 5*a*: Construction of pXL2647 and pXL2675.

Figure 6:
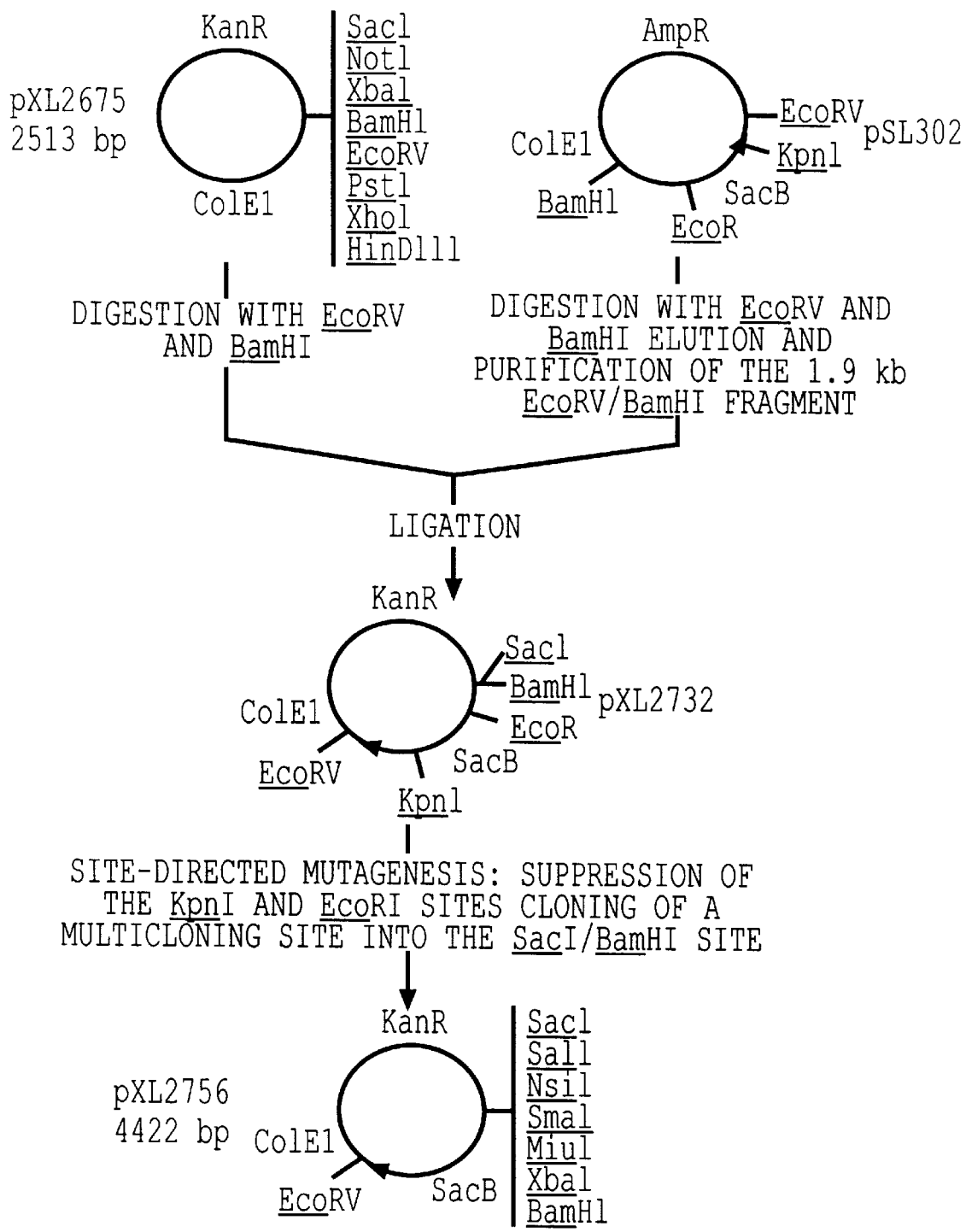

FIG. 6: Construction of pXL2756.

Figure 7:
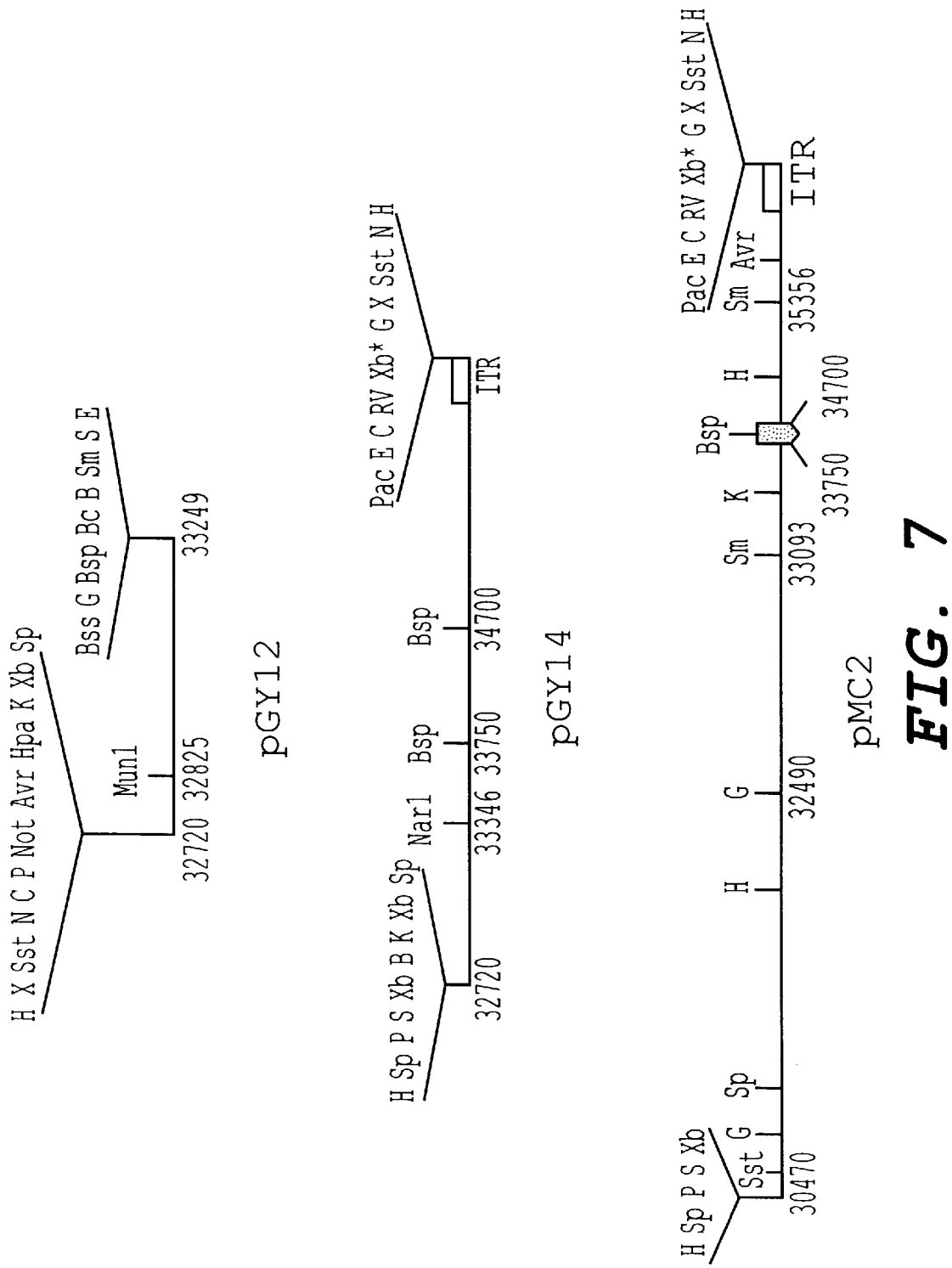

FIG. 7: Restriction endonuclease recognition sites in pGY12, pGY14, and pMC2.

FIG. 8: Restriction endonuclease recognition sites in pPY61, pPY6, and pPY13.

FIG. 9: Maps of pYJ3, pXL2756, and pYJ6.

FIG. 10: Restriction endonuclease recognition sites in pGY71, pCT1, pCT2, and pCT3.

Figure 11:
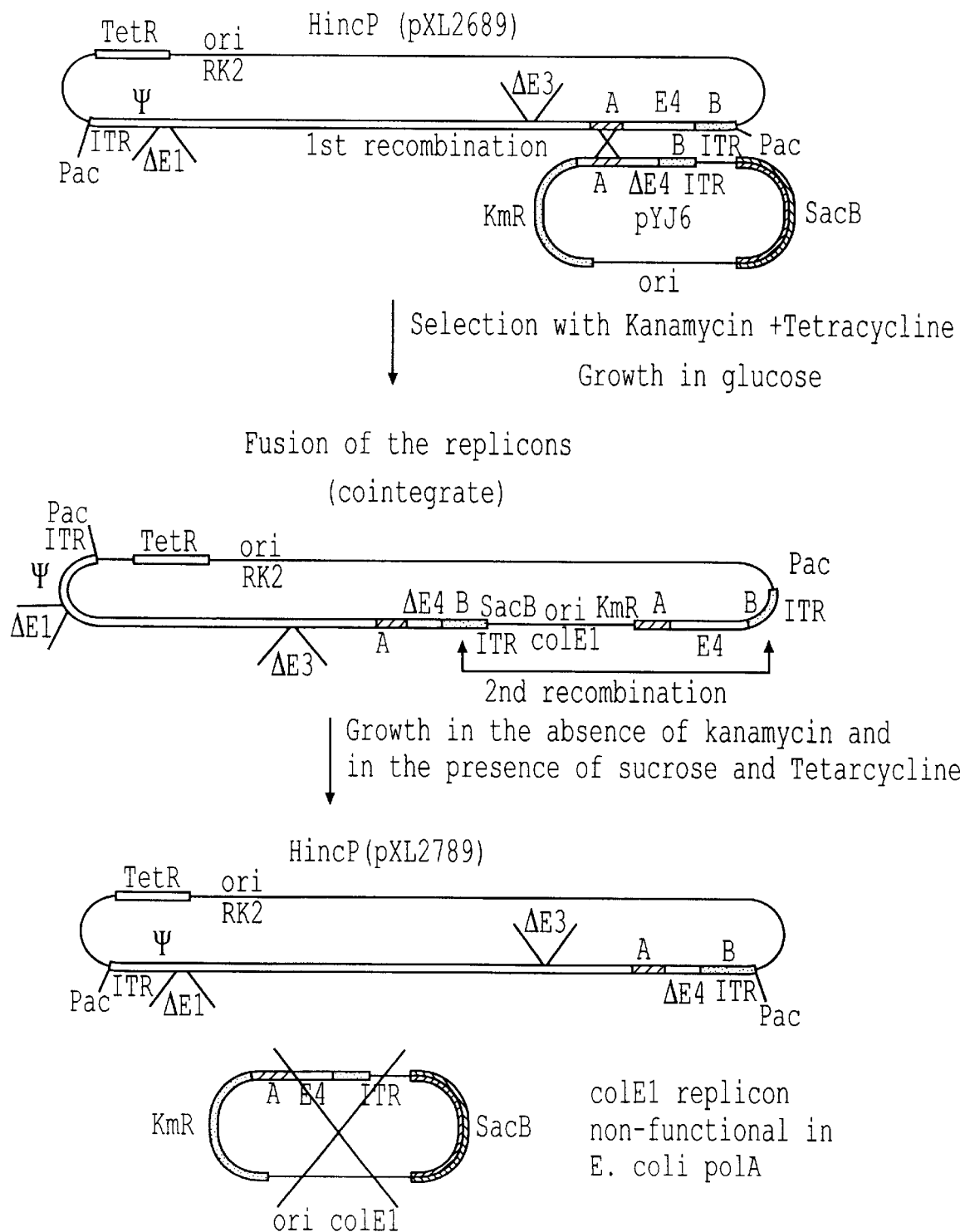

FIG. 11: Double recombination between pXL2689 and pYJ6.

FIG. 12*a*: Random deletions of the E4 region which are generated with Exolll.

FIG. 12*b*: Random deletions of the E4 region which are generated with Bal31.

Figure 13:
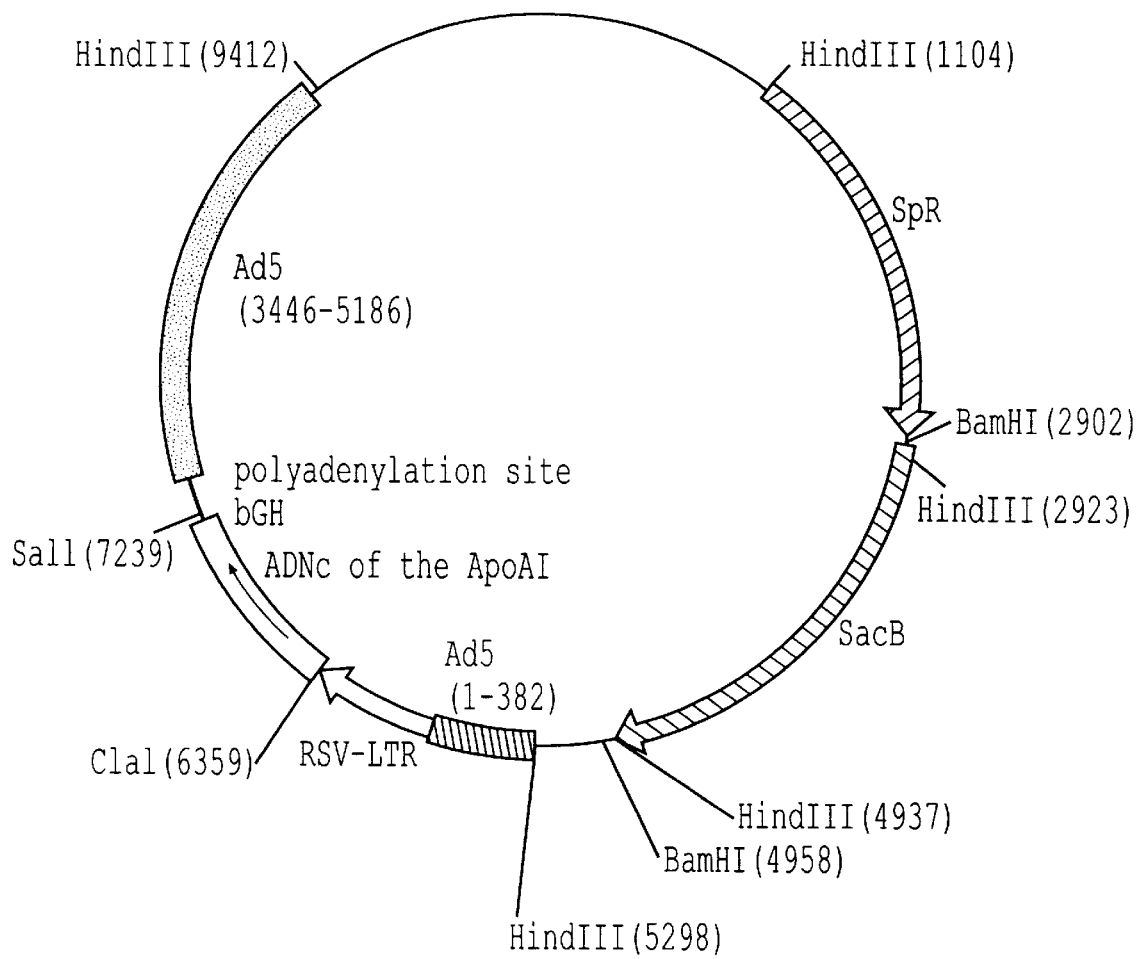

FIG. 13: Plasmid comprising ADNc of the ApolAl and the polyadenylation site from bovine growth hormone.

Figure 14:
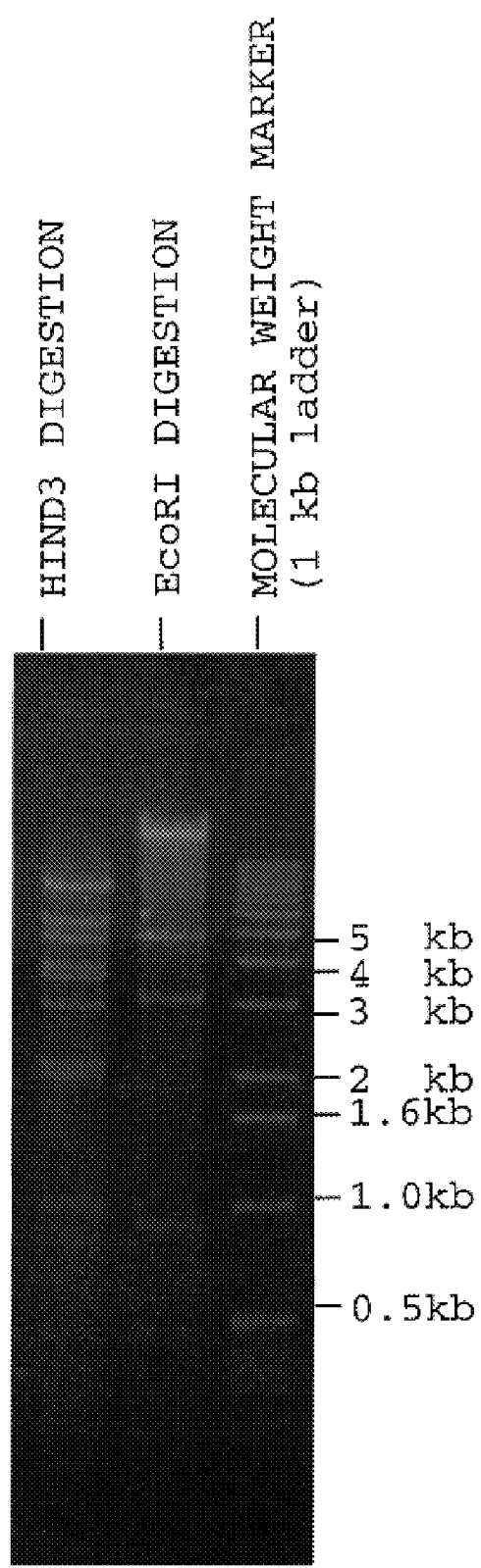

FIG. 14: Gel separation of Hind III and Eco RI restrication fragments.

FIG. 15: Generation of infectious viral genome.

FIG. 16: Maps of pGY57, pGY39, and pGY52.

General molecular biological and cloning technigues.

The standard molecular biological methods such as the centrifugation of plasmid DNA in a caesium chloride/ethidium bromide gradient, digestions using restriction enzymes, gel electrophoresis, transformation into *E. coli*, precipitation of nucleic acids, etc., are described in the literature (Maniatis et al., 1989).

The enzymes were supplied by New-England Biolabs (Beverly, Mass.). For the ligations, the DNA fragments are separated according to their size on 0.8 to 1.5% agarose gels, purified using GeneClean (BIO101, LaJolla Calif.) and incubated at 14° C. overnight in a 50 mM tris-HCl, pH 7.4, 10 mM MgCl$_2$, 10 mM DTT, 2 mM ATP buffer in the presence of T4 DNA ligase.

The ligated DNAs are used to transform the strain *E. coli* TG1[D(lac proA.B), supE, thi,hsdD 5/F traD 36, proA$^+$, B$^+$, lacI$^q$, lacZDM15] (Maniatis et al., 1982), which has been rendered competent, or else the strain *E. coli* polA SF800 (Heffron et al., 1977). sAmplification by PCR (polymerase chain reaction) was also carried out as described by Maniatis et al., 1989, with the following specifications:

Concentration of MgCl$_2$ brought to 8 mM.

Denaturation temperature 95° C., hybridization temperature 55° C., elongation temperature 72° C. This cycle was repeated 25 times in a PE9600 thermal cycler (Perkin Elmer, Norwalk Colo.).

The oligonucleotides are synthesized using phosphoramidite chemistry, with β-protection with a cyanoethyl group (Sinha et al., 1984, Giles 1985), using an Applied Biosystems model 394 automatic DNA synthesizer (Applied Biosystems, Foster City Calif.), in accordance with the manufacturer's recommendations.

The sequencing was carried out on double-stranded templates by means of the chain-termination method using fluorescent primers. We used the Taq Dye Primer sequencing kit from Applied Biosystems (Applied Biosystems, Foster City Calif.) in accordance with the manufacturer's specifications.

EXAMPLE 1

Cloning a human type 5 adenovirus genome, flanked by unique restriction sites, into an incompatibility group P plasmid which replicates in *E. coli*.

EXAMPLE 1-1

This example illustrates how the ends of the adenoviral genome can be amplified by PCR in such a way as to flank the ends (ITR) with a PacI site.

In order subsequently to obtain satisfactory recombination frequencies, we chose fragments of approximately 400 bp which were amplified. Three oligonucleotides were selected:

Oligo 1 is common to the two amplifications since it corresponds to the ends of the ITRs.

The six first nucleotides constitute a tail which avoids the formation of secondary structures. The six following nucleotides constitute an EcoRI restriction site which is employed for the intermediate cloning steps. The eight following nucleotides create a PacI site which is not present in the Ad5 genome (the sequence of adenovirus Ad5 is available in Genebank, mnemonic ADRCOMPGEN). The following twenty-seven nucleotides correspond to the left-hand end of the Ad5 genome, positions 1 to 27.

```
5'-CGGCGGGAATTCTTAATTAACATCATCAATAATATACCTTATTTTGG-3'   SEQ ID NO:1
         ---------------
         EcoRI    PacI
```

The use of oligo 3 together with oligo 1 results in the amplification of a fragment of 384 bp at the left-hand end. It encompasses a tail of six nucleotides. The eighteen following nucleotides create PstI, KPnI and SPeI sites. The twenty-four subsequent nucleotides correspond to the reverse complement of the selected Ad5 sequence between positions 361 and 385.

```
5'-CACCACCTGCAGGGTACCACTAGTGTCTCCACGTAAACGGTCAAAGTC-3' SEQ ID NO:3
          ------------------
           PstI    KpnI    SpeI
```

The template which is chosen for amplifying the left-hand end is the plasmid pCLAI. Plasmid pCLAI contains the left-hand end in the form of an EcoRI/XbaI fragment of 454 bp which is cloned into pIC19H.

The use of oligo 2 together with oligo 1 results in the amplification of a fragment of 418 bp at the right-hand end. It encompasses a tail of six nucleotides. The six following nucleotides create a PstI site. The subsequent twenty-four nucleotides correspond to the selected Ad5 sequence between positions 35517 and 35540.

```
                                        SEQ ID NO:2
5'-CACCACCTGCAGGGCAGCCATAACAGTCAGCCTTACC-3'
          ------
           PstI
```

The template which is chosen for amplifying the right-hand end is the plasmid pY23. Plasmid pY23 contains the right-hand end in the form of an AvrII/BClI fragment of 470 bp which is cloned into the compatible XbaI/BamHI sites of pIC19H.

The PCR products were loaded onto an agarose gel. The fragments of expected size were digested with EcoRI and PstI, purified and ligated in the presence of pUC19, which was digested with EcoRI and PstI. The two recombinant plasmids which were obtained were designated pXL2623, for the left-hand end, and pXL2624, for the right-hand end. The absence of any mutation in the insert was verified by sequencing. The EcoRI/PstI fragments from these plasmids were purified as previously described. The two fragments were brought together by ligating them into pUC19, which was linearized with EcoRI. The recombinant plasmid which is obtained is designated pXL2626; it contains the Ad5 ends in head-to-head orientation. (FIG. 2).

EXAMPLE 1–2

Construction, in E. coli, of a plasmid which contains the adenoviral ΔE1, ΔE3 genome flanked by PacI sites.

The vector used for receiving the adenoviral genome is pRK290 (Ditta et al., 1980), which belongs to incompatibility group P. This vector replicates in E. coli polA strains. The integration strategy employed is homologous recombination, in the strain E. coli SF800, between pXL2627 and the plasmid pFG144, (Graham et al., 1986). Plasmid pFG144 contains all of the Ad5 genome apart from two deletions in the E1 and E3 regions. It is derived from pMX2 and possesses the gene for resistance to ampicillin as well as a pMB1 origin of replication which does not allow it to replicate in the E. coli SF800 strain.

In the first instance, the head-to-head ends of the Ad5 genome were cloned into the unique EcoRI site of pRX290 using the protocol which has already been described for constructing pXL2626. Cells of the E. coli SF800 strain were rendered competent and transformed with pXL2627. The cultures were spread on LB medium in the presence of tetracycline. In their turn, the cells derived from a tetracycline-resistant clone were rendered competent, transformed with plasmid pFG144 and then spread on LB medium in the presence of tetracycline and ampicillin. Given that this plasmid does not replicate in the E. coli SF800 strain, acquisition of resistances to tetracycline and ampicillin can only take place by means of a homologous recombination event between the two plasmids. Thus, these two plasmids have in common the right-hand, 418 bp, and left-hand, 384 bp, ends of the Ad5 genome. The plasmids which result from this first recombination event possess two sets of ends. (FIG. 2). A second crossing-over, internally in the plasmid, can therefore take place. In this case, of the two possible events, only one leads to the desired construct, with the other resulting in the complete deletion of the Ad5 genome and the loss of the gene for resistance to ampicillin. This second recombination was favoured by a series of culture dilutions, representing 60 generations, in LB medium supplemented with tetracycline and ampicillin. The DNA from isolated clones was subjected to Southern blot analysis. The following oligonucleotide probe was synthesized:

5'-CGTGGAGACACTAGTGGTACCCTGCAGGGCA
GCCATA-3'                        SEQ ID NO:4

Bases 1 to 9 correspond to the left-hand region of position 377 to 385 in the Ad5 sequence. Bases 28 to 36 correspond to the sequence of the right-hand region between positions 35517 and 35525. Digestions with endonucleases PacI and ClaI, and also PacI and NdeI, demonstrated the expected plasmid structure. A clone which corresponded to such an event and which had the plasmid structure depicted in FIG. 3 was retained. This was designated pXL2628.

pXL2628 was digested with XbaI, religated and then transformed into competent E. coli TG1 cells. A clone which was $Tet^R$ and $Amp^S$ was retained. Its restriction profile demonstrates that the region corresponding to pMX2 was deleted. This clone was designated pXL2638. Digestion of pXL2638 with PacI releases the Ad5 genome in the form of a 34 kb fragment. This fragment can be employed as such for experiments in which it is used to transfect mammalian cells which are transcomplementing for the E1 functions of the adenovirus.

EXAMPLE 2

Production of recombinant adenoviruses

Clones of recombinant adenoviruses can be constructed, in a first step in Escherichia coli, by means of inserting fragments containing one or more genes, together with appropriate regulatory signals for expressing these genes in the mammalian cells under study, or by means of deleting certain fragments from the genome of the adenovirus, or else combining these two events; following this, a stock of such a recombinant virus can be obtained after producer cells have been transfected.

Plasmid pXL 2638 is purified from a culture of transformed, competent E. coli TG1 cells. The adenoviral genome is released by digesting in the presence of the enzyme PacI. The digestion product is used directly for producing the recombinant adenoviruses. To do this, the cells of line 293 are transfected with the digestion product from pXL2638 in the presence of calcium phosphate. The recombinant adenoviruses which are produced are then selected by plaque purification. Following isolation, the recombinant adenovirus is amplified in cell line 293, resulting in a culture supernatant which contains the unpurified recombinant adenovirus at a titre of approximately $10^{10}$ pfu/ml.

The viral particles are subsequently purified by centrifugation on a caesium chloride gradient in accordance with known techniques (see, in particular, Graham et al., Virology 52 (1973) 456). The adenovirus can be stored at −80° C. in 20% glycerol.

LITERATURE REFERENCES

Ausubel et al., 1987. Current protocols in molecular biology 1987–1988. John Wiley and Sons, New York.
Bolivar et al., 1977. Gene 2:95.
Dagert et al., 1979. Gene, 6, 23–28.
Ditta et al., 1980. Plasmid, 13, 149–154.
Ghosh-Choudhurry et al. 1986. Gene, 5b, 161–171.
Hamilton et al., 1989. J. Bacteriol. 171:4617–4622.
Hanahan, D. 1983. J. Mol. Biol. 166:557.
Heffron et al., 1977. Proc. Natl. Acad. Sci. USA, 74, 702–706.
Maniatis T., et al. 1982. Molecular Cloning: A Laboratory Manual, Cold Spring Harbor laboratory, New York.
Miller et al., 1988. J. Bacteriol. 170:2575–2583.
Simoes et al. 1991. New York Acad. Sci. 646:254–258.
Sinha N.D. et al. 1984. Nucl. Acids Res., 12, 4539–4557.
Slater et al. 1993. J. Bacteriol. 175:4260–4262.
Viera et al., 1982. Gene, 19, 259–268.
Wirth et al., 1989. Mol. Gen. Genet., 216, 175–177.
Zeef et al., 1994. EMBO J. 13:5113–5120.

What is claimed is:

1. A prokaryotic plasmid comprising an adenoviral genome flanked by one or more restriction sites not present in said genome, wherein the adenoviral genome is uninterrupted by a prokaryotic plasmid sequence.

2. The prokaryotic plasmid according to claim 1, further comprising a region enabling replication in a prokaryotic cell.

3. The plasmid according to claim 1, wherein the region enabling replication comprises an origin of replication functional in a prokaryotic cell.

4. The plasmid according to claim 3, wherein the origin of replication is derived from a bacterial plasmid selected from the group consisting of RK2, pBR322, and pUC.

5. The plasmid according to claim 2, further comprising a region enabling a prokaryotic cell comprising said plasmid to be selected.

6. The plasmid according to claim 1, wherein the adenoviral genome comprises ITR sequences and an encapsidation sequence.

7. The plasmid according to claim 6, wherein the adenoviral genome lacks all or part of an adenoviral E1 region.

8. The plasmid according to claim 7, wherein the adenoviral genome lacks a part of the adenoviral E1 region comprising residues 454 to 3328 or residues 382 to 3446.

9. The plasmid according to claim 7, wherein the adenoviral genome lacks all or part of an adenoviral E4, E3, or Iva2 region.

10. The plasmid according to claim 9, wherein the adenoviral genome lacks a part of the E4 region comprising adenoviral E4 ORF3 or ORF6 open reading frame.

11. The plasmid according to claim 1, wherein the adenoviral genome is of human or animal origin.

12. The plasmid according to claim 11, wherein the adenoviral genome is a human type 2 or type 5 adenoviral genome.

13. The plasmid according to claim 11, wherein the adenoviral genome is a canine CAV2 adenoviral genome.

14. The plasmid according to claim 1, wherein the adenoviral genome is an Ad5 adenovirus and is flanked by PacI, NspV, or SwaI restriction sites.

15. The plasmid according to claim 1, wherein the adenoviral genome comprises a nucleic acid of interest.

16. A plasmid, comprising an origin of replication of plasmid RK2, a gene encoding tetracycline resistance, and an uninterrupted adenovirus genome flanked by two PacI sites and having non-functional adenoviral E1 and E3 regions.

17. A prokaryotic cell comprising the plasmid according to claim 1.

18. A process for producing a recombinant adenoviral genome comprising culturing the prokaryotic cell according to claim 17, and recovering the plasmid from said cell.

19. The process according to claim 18, further comprising treating the plasmid to excise the adenoviral genome.

20. The process according to claim 19, further comprising treating the plasmid with a restriction enzyme corresponding to the restriction sites flanking the adenoviral genome.

21. The process of claim 18 further comprising transfecting an encapsidating cell line with the recombinant adenoviral genome to produce a recombinant adenovirus.

22. The process according to claim 21, wherein the encapsidating cell line is cell line 293.

* * * * *